United States Patent
Zhou

(10) Patent No.: US 9,594,080 B2
(45) Date of Patent: Mar. 14, 2017

(54) MOLECULAR RECOGNITION MATRIX AND METHOD FOR MAKING SAME

(76) Inventor: Yanxiu Zhou, Phoenix, AZ (US)

(*) Notice: Subject to any disclaimer, the term of this patent is extended or adjusted under 35 U.S.C. 154(b) by 296 days.

(21) Appl. No.: 12/694,088

(22) Filed: Jan. 26, 2010

(65) Prior Publication Data

US 2010/0226984 A1  Sep. 9, 2010

Related U.S. Application Data

(60) Provisional application No. 61/209,652, filed on Mar. 9, 2009.

(51) Int. Cl.
*G01N 33/543* (2006.01)

(52) U.S. Cl.
CPC .................. *G01N 33/54386* (2013.01)

(58) Field of Classification Search
CPC ................................................ G01N 33/54386
See application file for complete search history.

(56) References Cited

U.S. PATENT DOCUMENTS

| | | | |
|---|---|---|---|
| 6,310,110 B1* | 10/2001 | Markowitz et al. | 521/99 |
| 6,458,599 B1* | 10/2002 | Huang | B01J 20/268 427/2.13 |
| 6,582,971 B1* | 6/2003 | Singh et al. | 436/518 |
| 7,393,909 B2 | 7/2008 | Sellergren et al. | |
| 2003/0139483 A1* | 7/2003 | Markowitz et al. | 521/99 |
| 2003/0153001 A1* | 8/2003 | Soane et al. | 435/7.1 |
| 2004/0058380 A1 | 3/2004 | Levon et al. | |
| 2004/0157209 A1* | 8/2004 | Yilmaz | B01J 20/26 435/5 |
| 2008/0102532 A1* | 5/2008 | Deevi et al. | 436/107 |
| 2008/0179191 A1 | 7/2008 | Zhou et al. | |
| 2009/0087549 A1 | 4/2009 | Zhou et al. | |
| 2009/0197297 A1* | 8/2009 | Murray | G01N 21/78 435/29 |

FOREIGN PATENT DOCUMENTS

WO  2005/059507 A2  6/2005

OTHER PUBLICATIONS

Yanxiu Zhou et al., Potentiometric Sensing of Chemical Warfare Agents: Surface Imprinted Polymer Integrated with an Indium Tin Oxide Electrode, Anal. Chem. 2004, 76, 2689-2693.
Yanxiu Zhou et al., Potentiometric Sensing of Chiral Amino Acids, Chem. Mater. 2003, 15, 2774-2779.
Yanxiu Zhou et al., Potentiometric sensor for dipicolinic acid, Biosensors and Bioelectronics 20 (2005) 1851-1855.
Yantian Wang et al., A potentiometric protein sensor built with surface molecular imprinting method, Biosensors and Bioelectronics 24 (2008) 162-166.
Steven C. Zimmerman et al., Synthetic hosts via molecular imprinting—are universal synthetic antibodies realistically possible?, Chem. Commun. 2004, 5-14.
(Continued)

*Primary Examiner* — Melanie Y Brown
(74) *Attorney, Agent, or Firm* — Zeman-Mullen & Ford, LLP

(57) ABSTRACT

A molecular recognition matrix which utilizes the interaction between molecular building blocks and the surface of a substrate to develop specific molecular recognition cavities.

14 Claims, 5 Drawing Sheets

(56) References Cited

OTHER PUBLICATIONS

John Anderson, et al., Steady-State and Frequency-Domain Lifetime Measurements of an Activated Molecular Imprinted Polymer Imprinted Dipicolinic Acid, Journal of Fluorescence, vol. 14, No. 3, May 2004.

Yun-Mei, et al., Synthesis and Evaluation of Molecularly Imprinted Polymers Using Acetylsalicylic Acid as Template, Journal of Instrumental Analysis, vol. 26, No. 2, 165-169.

Claudio Baggiani, Adsorption isotherms of a molecular imprinted polymer prepared in the presence of a polymerisable template Indirect evidence of the formation of template clusters in the binding site, Analytica Chimica Acta 504 (2004) 43-52.

Roongnapa Suedee, et al., Development of trichloroacetic acid sensor based on molecularly imprinted polymer membrane for the screening of complex mixture of haloacetic acids in drinking water, Analytica Chimica Acta 504 (2004) 89-100.

C. Baggiani, et al., Binding properties of 2,4,5-trichlorophenoxyacetic acid-imprinted polymers prepared with different molar ratios between template and functional monomer, Talanta 62 (2004) 1029-1034.

Hye-Ryoung Park, et al., Separation of Hydroxybenzoic Acid Isomers Using the Molecular Imprinting Technique, Journal of Applied Polymer Science, vol. 105, 2824-2829 (2007).

Huiting Zhang, et al., Retention behavior of phenoxyacetic herbicides on a molecularly imprinted polymer with phenoxyacetic acid as a dummy template molecule, Bioorganic & Medicinal Chemistry 15 (2007) 6089-6095.

Koji Nemoto, et al., Simple and Effective 3D Recognition of Domoic Acid Using a Molecularly Imprinted Polymer, J. Am. Chem. Soc. 2007, 129, 13626-13632.

Karsten Haupt, et al., Assay System for the Herbicide 2,4-Dichlorophenoxyacetic Acid Using a Molecularly Imprinted Polymer as an Artificial Recognition Element, Anal. Chem. 1998, 70, 628-631.

C. Baggiani, et al., Chromatographic characterization of molecularly imprinted polymers binding the herbicide 2,4,5-trichlorophenoxyacetic acid, Journal of Chromatography A, 883 (2000) 119-126.

Claudio Baggiani, et al., Molecularly imprinted solid-phase extraction sorbent for the clean-up of chlorinated phenoxyacids from aqueous samples, Journal of Chromatography A, 938 (2001) 35-44.

Hui Li, et al., Separation and purification of chlorogenic acid by molecularly imprinted polymer monolithic stationary phase, Journal of Chromatography A, 1098 (2005) 66-74.

K.P. Prathish, et al., Molecularly imprinted polymer-based potentiometric sensor for degradation product of chemical warfare agents Part I. Methylphosphonic acid, Talanta 71 (2007) 1976-1980.

Yu Ping Zhang, et al., Novel preparation of monolithic imprinted columns for electrochomatographic separation by photopolymerization, Chinese Chemical Letters 18 (2007) 734-737.

Yongjian Wang, et al., Specific binding of cholic acid by crosslinked polymers prepared by the hybrid imprinting method, Polymer 48 (2007) 5565-5571.

Hsin-Hung Pan, et al., Synthesis of Molecularly Imprinted Polymer and its Molecular Recognition Properties of N-Acetylneuraminic Acid, E-Journal of Chemistry, vol. 4, No. 4, pp. 611-619, Oct. 2007.

Yun-Mei, et al., Synthesis and Evaluation of Molecularly Imprinted Polymers Using Acetylsalicylic Acid as a Template, Journal of Instrumental Analysis, vol. 26, No. 2, 165-169.

* cited by examiner

MOLECULAR RECOGNITION MATRIX AND METHOD FOR MAKING SAME

CROSS-REFERENCE TO RELATED APPLICATIONS

This application claims the benefit of U.S. Provisional Application No. 61/209,652, filed Mar. 9, 2009 which is herein incorporated by reference in its entirety.

FIELD OF INVENTION

The present invention relates to a molecular recognition matrix and method for making the same. More particularly, the present invention relates to a molecular recognition matrix that is based on the interaction of molecules, or molecule building blocks, with the surface of substrates. The method of the present invention for making a molecular recognition matrix can be used as a method or process for making universal man-made antibodies.

BACKGROUND OF THE INVENTION

Molecular imprinting is a known technique for making synthetic hosts which are the man-made mimics of biological receptors or enzymes that possess sites for molecular recognition and catalysis. Molecular imprinting involves creating template-shaped cavities in polymer matrices with the memory of the template molecules used for molecular recognition. This system is based on the "lock and key" model which is the system used by enzymes for substrate recognition. Enzymes have active binding sites with a unique geometric structure which selectively bind to a substrate having a corresponding shape.

In prior art molecular imprinting processes, substrate-selective recognition sites are prepared in a matrix using a casting procedure with a template molecule. Functional monomers attach to, or assemble around, a template molecule and the functional monomers and the template molecule are subsequently linked together by a cross-linking agent to form a molecularly imprinted polymer network. Removal of the template molecule from the molecularly imprinted polymer network creates a structure complementary to the template structure allowing its tight and selective uptake.

Despite the broad use of the above described molecular imprinting technique, there are inherent limitations with this process that decrease its practical suitability. For example, one inherent limitation is the inability for polymers to generate molecule size cavities with structure details due to the non-structure orientation around the templates and the macro-scale nature of the prior art molecular imprinting process. It is difficult to use a polymer as a building matrix to make molecule size recognition hosts. Another limitation is that the molecular recognition for sensor application is separated from transduction. For example, in nature, where there are ion channels in membranes, it is hard to distinguish molecular recognition from transduction, the two main components of sensors, as they are integrated and not separable. Other limitations and problems with the prior art molecular imprinting technique described above include heterogeneity in binding affinities, slow mass transfer in and out of the polymer matrix or network, overall low binding affinity, lack of a read-out for complexation, and slow template leaching.

Accordingly, there is a need for molecular recognition matrix that overcomes these limitations and problems and, in particular a need for a molecular recognition matrix that provides molecular recognition cavities with antibody-like ability to bind and discriminate between molecules or other structures.

SUMMARY OF THE INVENTION

In accordance with various aspects of the present invention, a molecular recognition matrix and methods for making the molecular recognition matrix are provided. In accordance with one exemplary embodiment, the molecular recognition matrix of the present invention is produced by a process of providing one or more molecules for use as molecule building blocks, providing a substrate having a surface capable of interacting with the molecule building blocks, providing one or more template molecules, providing one or more solvents to create a solvent solution, adding the molecule building blocks, the template molecules, and the substrate to the solvent solution to create a matrix, removing the matrix from the solvent solution which has since become a deposition solution, and rinsing the matrix with one or more solvents or other solutions to extract the template molecules thereby resulting in an imprinted substrate having a molecular recognition matrix. The imprinted substrate has one or more molecular recognition cavities formed on the surface of the substrate.

In one aspect of the present invention, the molecule building blocks may include monomers, molecules, ions, polyatomic ions, salts, compounds, complexes, pure chemical elements, elemental molecules, and/or crystals. In another aspect of the present invention the substrate may be a solid material that may include polymers, optical fibers, metals, semiconductors, glasses, plastics, organic materials, and/or inorganic materials. In addition, the substrate may take the form of any shape and may include any size of material from bulk size materials to nanometer size materials.

In still another aspect of the present invention, the template molecule or molecules may include small molecules, biological macromolecules, microorganisms, crystals, viruses, and/or any other material needing detection, separation, extraction, identification, adsorption, capturing or any other functional process. In still another aspect of the present invention, the interaction between the substrate surface and the molecular building blocks may include covalent bonding, non-covalent bonding, hydrophobic forces, van der walls forces, pi-pi interactions, ionic interactions, electrostatic force, and/or other interactions that keep the template molecule or molecules within the matrix formed within the deposition solution.

In another exemplary embodiment of the present invention, the imprinted substrate of the resulting molecular recognition substrate may be cured.

The present invention also includes a method for making a molecular recognition matrix which includes the steps of a) providing one or more molecules for use as molecule building blocks and a substrate having a surface capable of interacting with the molecule building blocks, b) providing one or more template molecules which may include providing more than one kind of template molecule, c) adding the molecule building blocks and the template molecules to one or more solvents to create a deposition solution, d) adding the substrate to the deposition solution to create a matrix via the interaction between the building blocks and the surface of the substrate, e) removing the substrate containing the matrix from the deposition solution, and f) rinsing the substrate containing the matrix with one or more solvents or other solutions to extract the template molecules and expose an imprinted substrate. In one exemplary embodiment of the present invention, the method for making a molecular recognition matrix may further include the step of synthesizing the molecule building blocks to have a specific function to interact with the surface of the substrate. In another exemplary embodiment of the present invention, the method for making a molecular recognition matrix may further include the step of pre-modifying or pre-treating the surface of the substrate with one or more specific functional groups that interact with the molecule building blocks. In yet another exemplary embodiment of the present invention, the method for making a molecular recognition matrix may further include the step of carrying out a post-synthetic functionalization process to increase the affinity and/or selectivity of the imprinted substrate after exposing the imprinted substrate.

Another exemplary embodiment of the method for making a molecular recognition matrix of the present invention includes the steps of a) providing one or more molecules for use as molecule building blocks, a substrate having a surface capable of interacting with the molecule building blocks, and one or more template molecules, which may include providing more than one kind of template molecule b) providing one or more solvents to create a solvent solution, c) adding the molecule building blocks, the substrate, and the template molecule(s), in any order, to the solvent solution to create a matrix via the interaction between the building blocks and the surface of the substrate, d) removing the substrate containing the matrix from the solvent solution which has since become a deposition solution, and e) rinsing the substrate containing the matrix with one or more solvents or other solutions to extract the template molecules and expose an imprinted substrate.

In addition, the methods of the present invention for making a molecular recognition matrix may include all of the aspects previously described above with respect to the molecular recognition matrix itself and the various components of the molecular recognition matrix.

The molecular recognition matrix of the present invention utilizes molecule size building blocks for the recognition matrix with specific structure orientation instead of polymers without any structure orientation (as done in the prior art) and employs the interaction between the molecule size building blocks and the surface of substrates to control the building block molecule orientation to define recognition cavities. As a result, specific molecule size recognition cavities can be formed.

Further aspects of the invention and areas of applicability will become apparent from the description provided herein. It should be understood that the description and specific examples are intended for purposes of illustration only and are not intended to limit the scope of the present invention.

BRIEF DESCRIPTION OF THE DRAWINGS

The drawings described herein are for illustration purposes only and are not intended to limit the scope of the present disclosure in any way. The present invention will become more fully understood from the detailed description and the accompanying drawings wherein.

DETAILED DESCRIPTION

Figure 1:
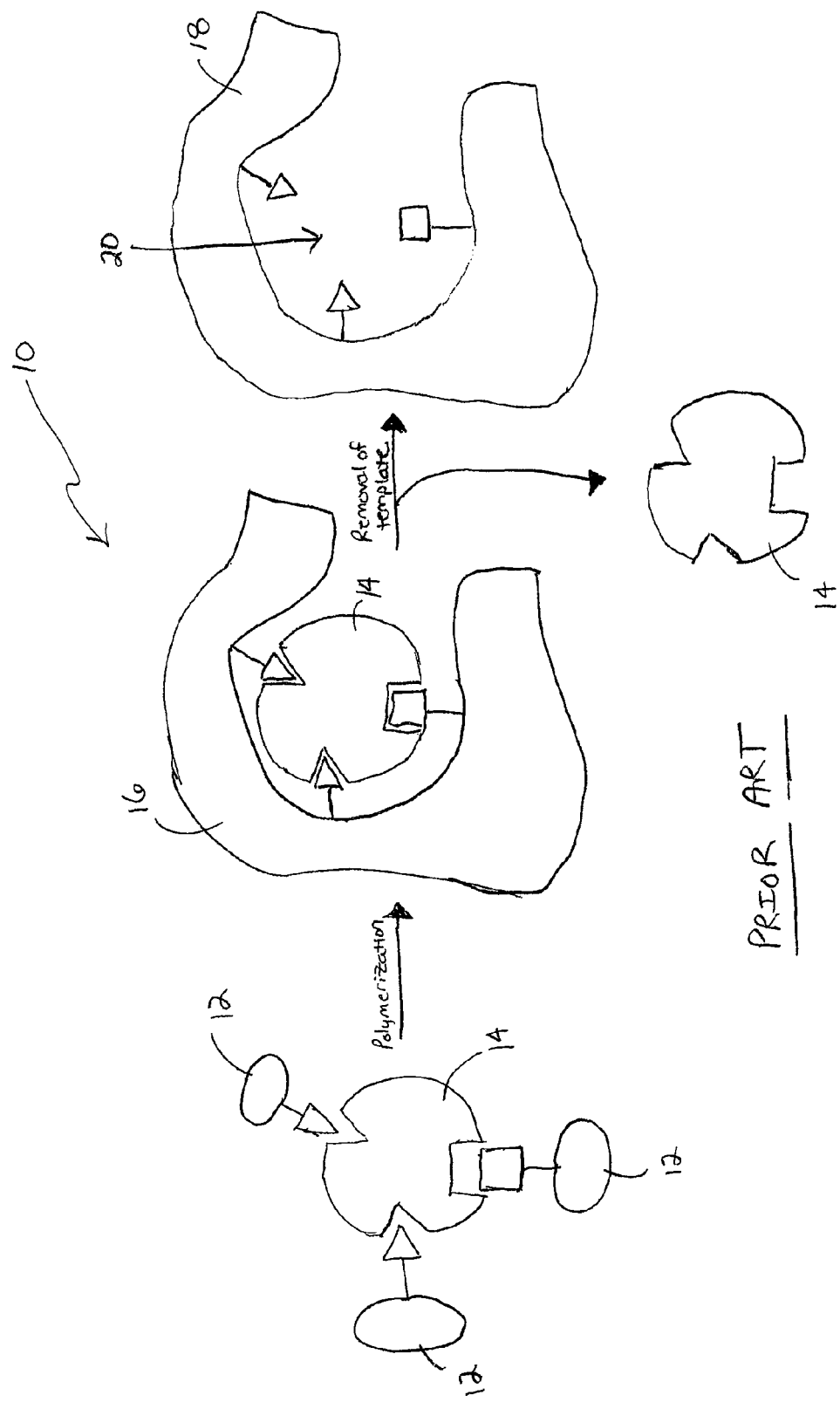
FIG. 1 is a diagram showing a prior art molecular imprinting technique.

The following description is merely exemplary in nature and is not intended to limit the present invention or its teachings, applications, or uses thereof. It should be understood that throughout the drawings, corresponding reference numerals indicate like or corresponding parts and features. The description of specific examples indicated in various embodiments and aspects of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features.

The present invention may be described herein in terms of various functional components and processing steps. It should be appreciated that such components and steps may be realized by any number of molecular components configured to perform the specified functions. For example, the present invention may employ molecule building blocks such as monomers, molecules, ions, salts, compounds, complexes, pure chemical elements, elemental molecules, crystals, and other types of building blocks to interact with the surface of a substrate such as a solid substrate in the presence of a deposition solution and a template molecule(s) to create a matrix.

FIG. 1 is a diagram showing a prior art molecular imprinting technique. The prior art molecular imprinting technique 10 includes functional monomers 12 which are self-assembled around a template molecule 14 by interaction between function groups on both the template molecule and monomers. The functional monomers 12 are then polymerized to form an imprinted matrix 16. The template molecule 14 is then removed from the polymer matrix 16 to leave behind an imprinted material 18 having a cavity 20 complementary in size and shape to the template 14. The cavity 20 works as a selective binding site for a specific template molecule. The prior art molecular imprinting technique utilizes covalent bonding or non-covalent bonding between the monomer and template to build the specific binding sites within the polymers. The present invention differs from the prior art molecular imprinting technique in that the present invention does not require bonding between the molecule building blocks and the templates. Instead the present invention focuses on the bonding or interaction of the molecule building blocks with the surface of substrates. The recognition matrix is generated during the self-assembling or other process of the molecule building blocks to the surface around the templates. This mimics the biological machinery and offers a great level of control over the structure of materials compared to the three-dimensional matrix due to high orientation of the structure, and allows this surface imprinting system to build template molecule structures in more detail.

The present invention uses the molecule interaction between molecules (used as building blocks for the recognition matrix) and a surface to generate molecular recognition pin holes on the surface. Unlike prior art molecular imprinting techniques, there is no specific bonding required between the monomers or molecules that act as building blocks and the template molecules. Instead, the present invention employs the interaction between the molecular building blocks and the surface of a substrate to develop the specific molecular recognition cavities. In particular, the molecules will self-assemble, polymerize, polymerize after self-assembling, electro-polymerize, or use other reactions to interact with the surface of substrates in the presence of templates, such as small molecules, biological macromolecules, microorganisms, whole crystals, viruses, and/or any other material needing detection, separation, extraction, identification, adsorption, capturing, or other any other functional process. Because there is no interaction between the templates and the surface of the substrate during the surface imprinting process, the templates are only physically trapped within the matrix on the surface of the substrate and can be easily washed away. Removal of the templates from the matrix generates a structure complementary to the template structure or to an analogous structure on the surface of substrates.

The present invention enables the creation of universal molecular recognition cavities because the interaction to build the recognition cavities is between the molecule and the surface of substrates, not between the molecules/monomers and templates. The present invention ensures that the building molecules assembled around the templates are oriented with a great level of control over the material's structure. The matrix resulting from the present invention still provides three dimensional recognition cavities but with one dimension as the substrate that is an open bottom with thin film cavities on it that will act as a filter to allow molecules with the same geometrical features of the displaced molecules to enter. This property assures the assessability for the subsequent recognition process. Accordingly, it can be subsequently used to detect molecular details in a more precise manner. Only the smallest building block molecules with specific orientation are able to form a matrix around the template molecules and copy their specific structure with detail.

Figure 2:
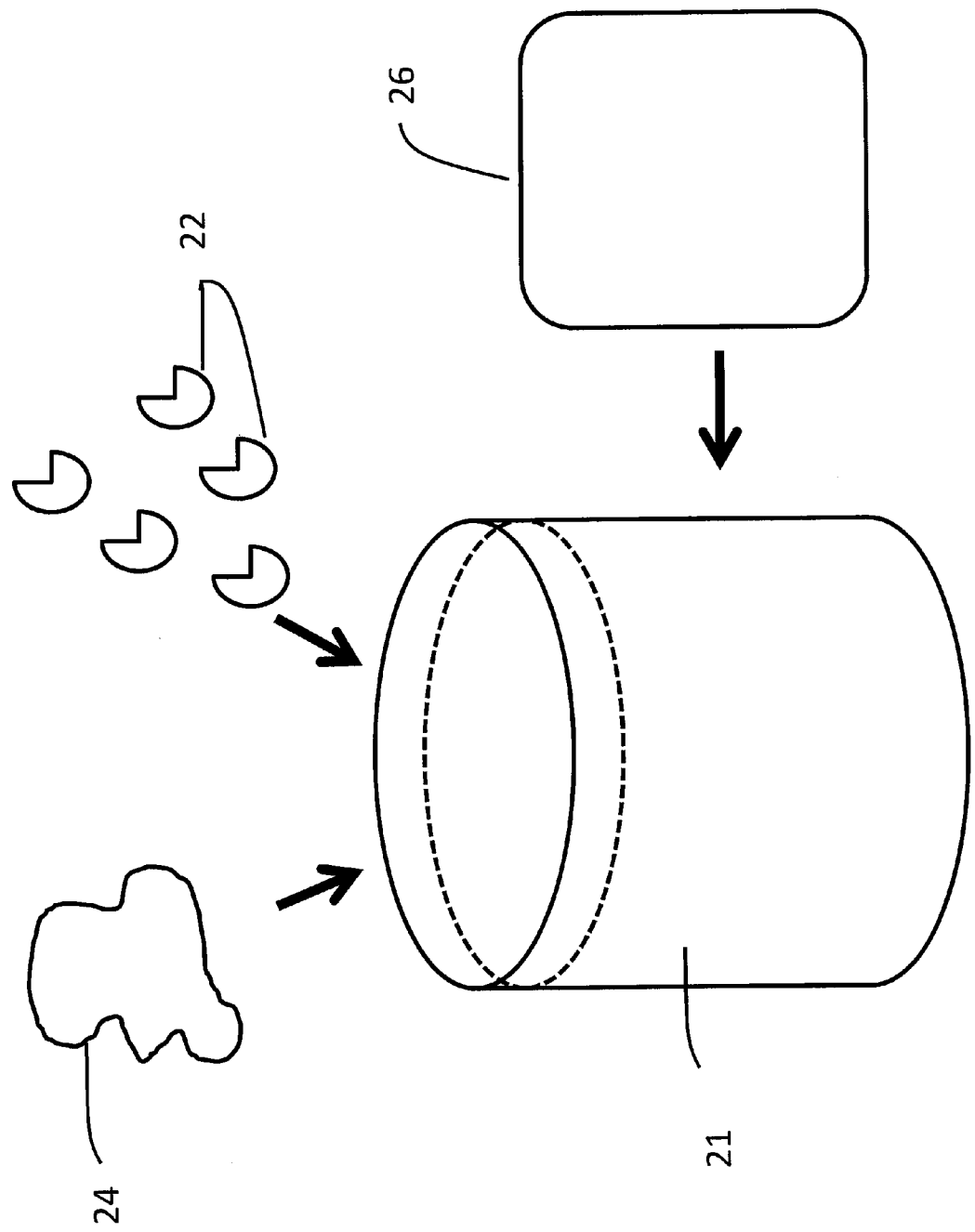
FIG. 2 is an illustration showing the components that are combined to create the molecular recognition matrix of the present invention.
Figure 3:
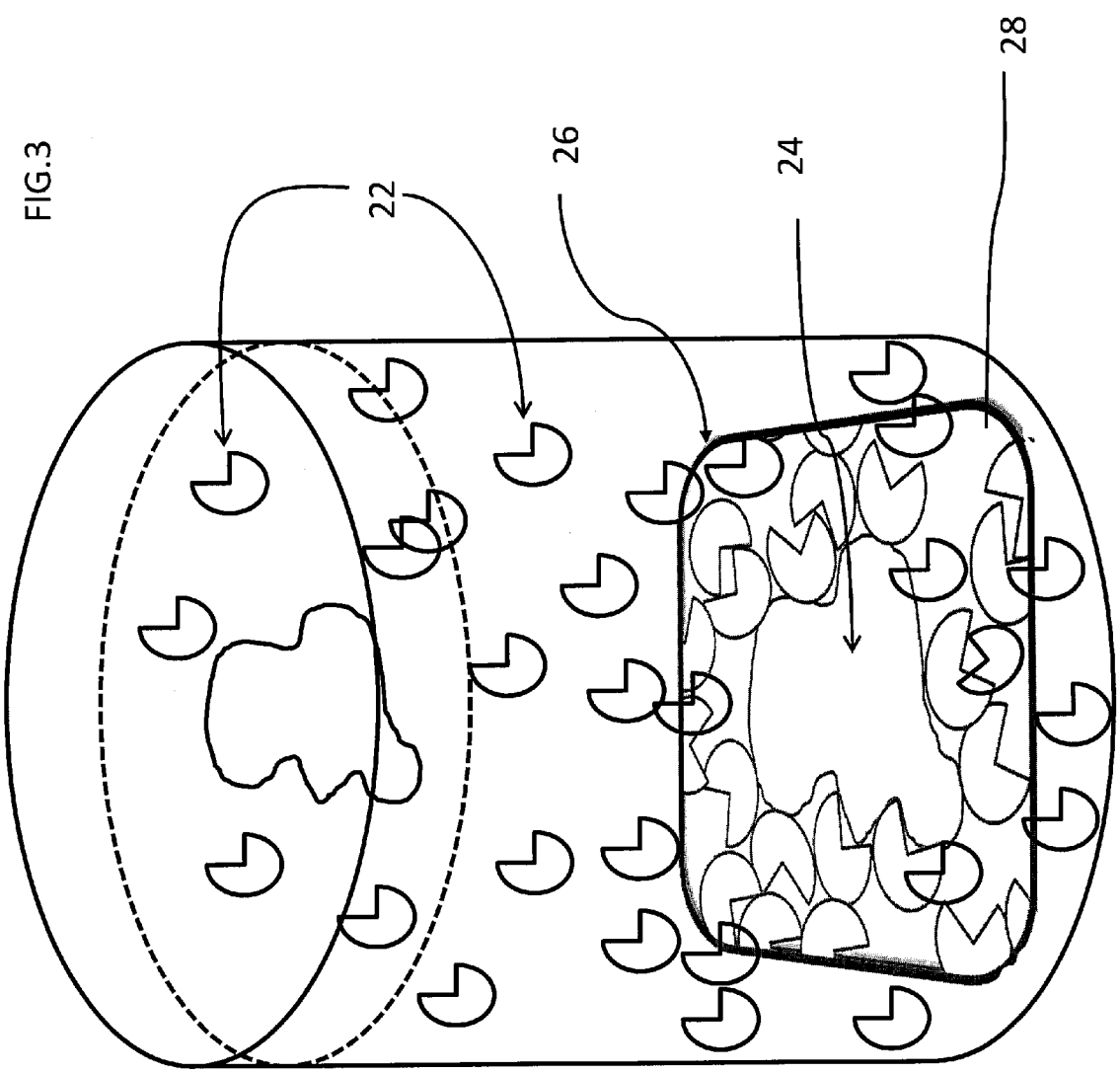
FIG. 3 is an illustration showing a matrix created by the interaction between the molecule building blocks and the surface of a substrate in the presence of a template molecule.

FIG. 2 is an illustration showing the components that are combined to create the molecular recognition matrix of the present invention. One or more solvents are combined to create a solvent solution 21. Molecule building blocks 22, one or more template molecules 24, and a substrate 26 having a surface capable of interacting with the molecule building blocks 22 are all added to the solvent solution 21. The molecule building blocks 22, the template molecule(s) 24, and the substrate 26 can be added to the solvent solution 21 in any sequence depending upon the imprinting system. FIG. 3 is an illustration showing a matrix 28 created by the interaction between the molecule building blocks 22 and the surface of the substrate 26 in the presence of the template molecule 24.

The molecules used for the molecule building blocks are carefully selected to interact with the surface of substrates to form a recognition matrix. The molecules should have functional groups that could react with the surface of substrates, or form a film on the surface of substrates, by self-assembling, polymerizing, polymerizing after self-assembling, or carrying out other reactions to interact with the surface of the substrate. The molecule building blocks may include monomers, molecules, ions, polyatomic ions, salts, compounds, complexes, pure chemical elements, elemental molecules, crystals, or any other molecular component that will interact with the surface of a substrate to form a recognition matrix. The interaction between the molecule building blocks and the surface of the substrate may include covalent bonding, non-covalent bonding, hydrophobic forces, van der walls forces, pi-pi interactions, ionic interactions, electrostatic interactions, and/or other interactions that keep the template molecule or molecules within the matrix formed within the deposition solution. The substrate may take the form of any shape such as planar, round, curved surfaces, etc. and may comprise any size of material from bulk size materials to the nanometer size materials. The substrate may be a solid material that may include polymers, optical fibers, metals, semi-conductors, glasses, plastics, organic materials, inorganic materials, and/or the like.

The solvent or solvents used to make the deposition solution must enable the molecule building blocks to interact with the surface of the substrate to form specific recognition cavities on the surface of the substrate in the presence of template molecules. The molecule building blocks should be soluble in the solvent or solvents. The template molecule could be soluble or insoluble in the deposition solution. The template molecule or molecules may include small molecules, biological macromolecules, microorganisms, crystals, viruses, and/or any other material needing detection, separation, extraction, identification, adsorption, capturing, or any other functional process.

Figure 4:
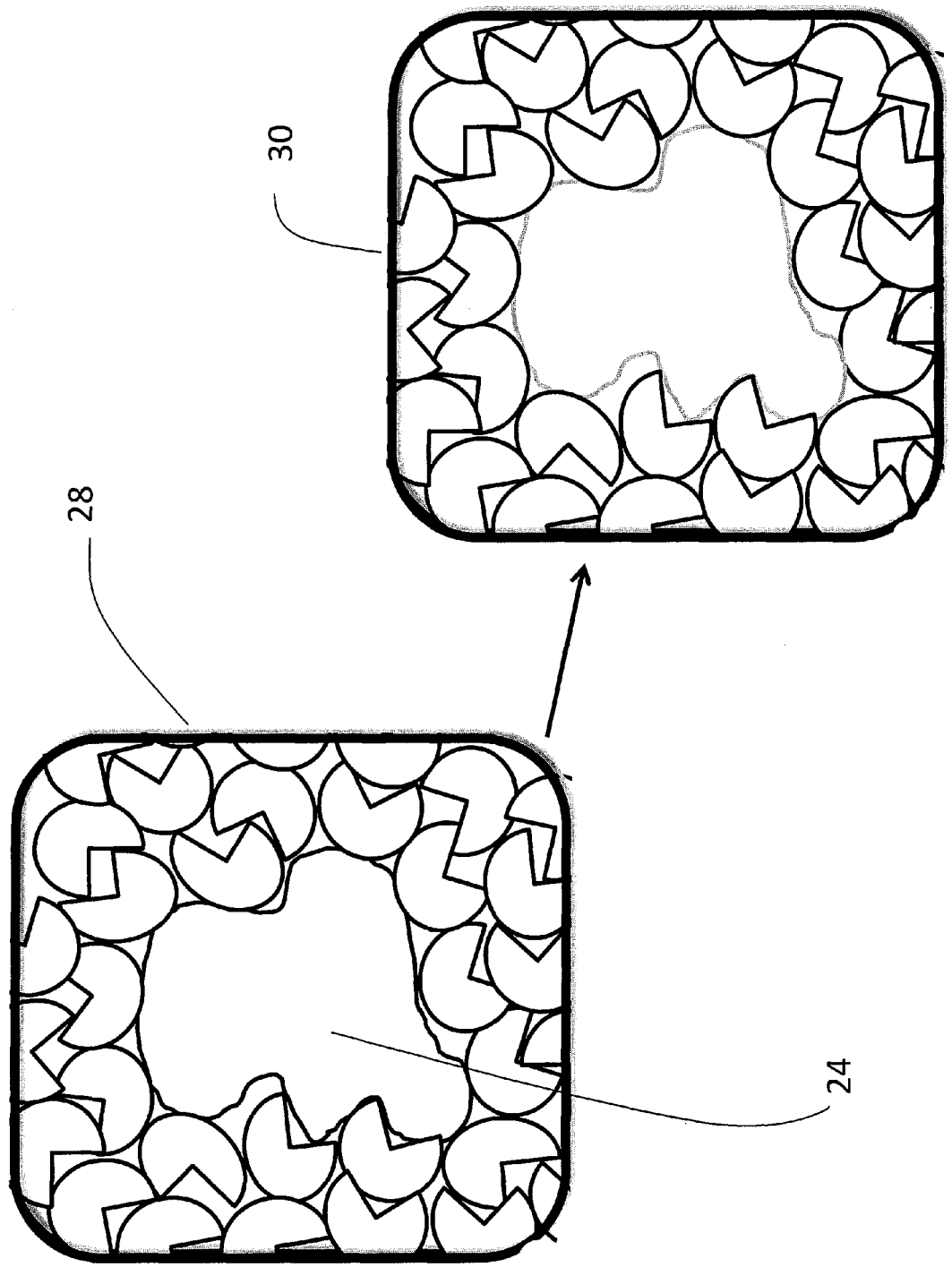
FIG. 4 is an illustration showing the rinsing of the matrix to remove the template molecule in order to create an imprinted substrate.

FIG. 4 is an illustration showing the rinsing of the matrix 28 to remove the template molecule 24 in order to create an imprinted substrate 30. The matrix 28 is rinsed with one or more solvents or other solutions that are able to extract the template molecules from the matrix. The template molecules are easily extracted out of the matrix.

With the present invention, there is no bonding required between the molecule building blocks and the templates so there is no need to carefully design the interactions, synthesize the functional monomers, or modify the templates. Accordingly, the present invention simplifies the imprinting process and allows the templates to be easily and more completely removed. The molecular recognition matrix of the present invention results in biological host like cavities that will bind to particular molecular structures strongly and specifically. In addition, the matrix generated by the present invention is two-dimensional with the other dimension being the surface of the substrate. Therefore, it will produce easy readout as soon as the molecules are able to enter the cavities if the surface of the substrate is a transducer. For application of a molecular recognition matrix of the present invention as a sensor, no coating process is needed since the recognition cavities are already built on the surface of the substrate. The molecular recognition matrix of the present invention simplifies the fabrication process and makes the transition of binding into an easy readout. For solid state extraction, separation, adsorption and other applications, the recognition cavity in the molecular recognition matrix of the present invention can be easily and efficiently accessed since the recognition cavities are built on the surface of substrates. This results in reducing the concentration time and increasing the binding kinetics. For synthesis methods, the molecular recognition matrix of the present invention is a high yielding imprinting method in that it only needs one or few steps to prepare highly specific recognition cavities. Since the matrix is on the surface of substrates and the building block molecules are bonded to the surface, the thickness of the film is controllable and can be very thin, sometimes as thin as a monolayer. This very thin film can be clearly produced and reproduced making it particularly applicable for the development of optical and acoustic sensors.

Figure 5:
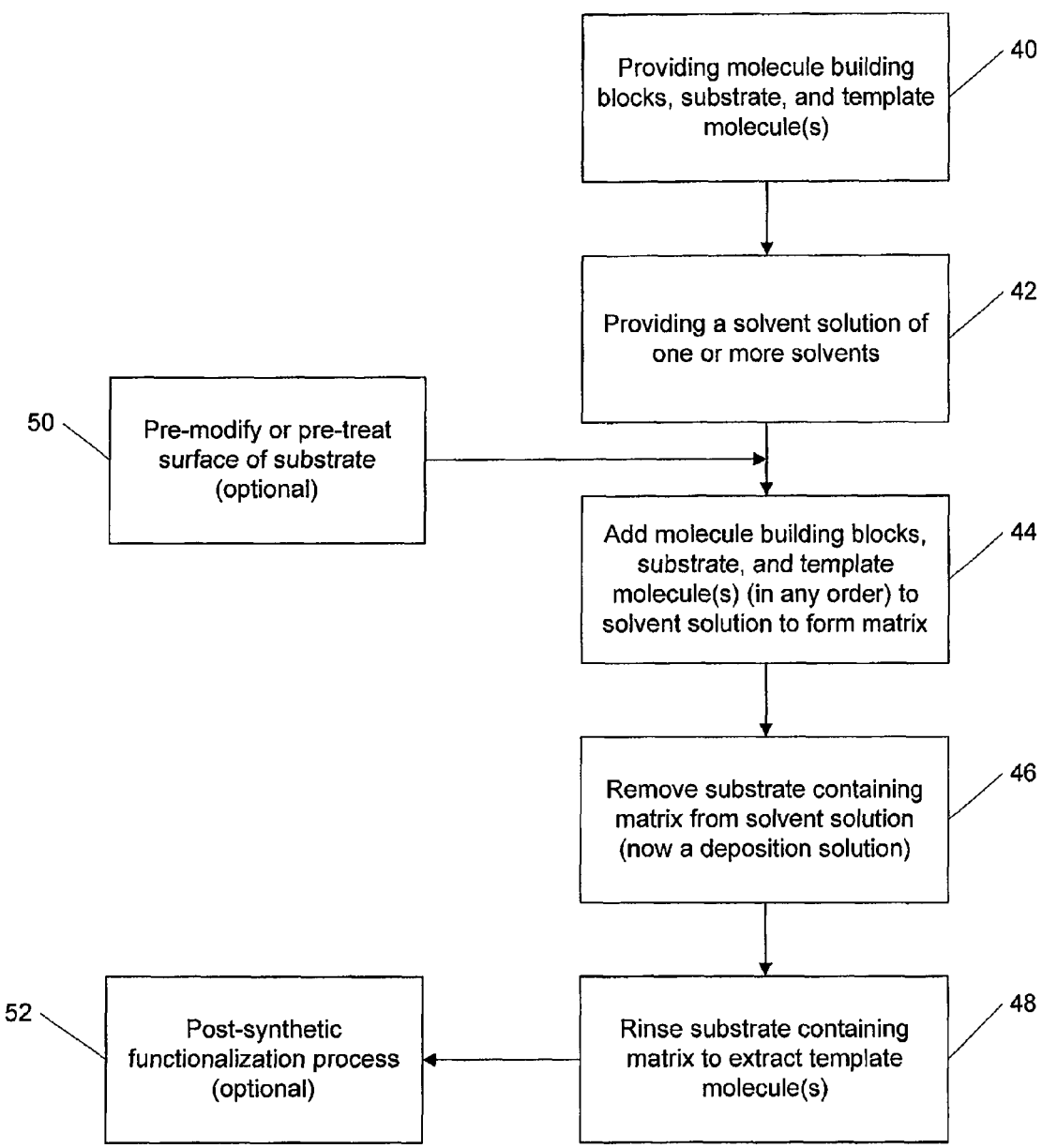
FIG. 5 is a flowchart showing an exemplary method of the present invention for making the molecular recognition matrix.

FIG. 5 is a flowchart showing an exemplary method of the present invention for making a molecular recognition matrix. First, in step 40, molecule building blocks, a substrate, and one or more template molecules are provided. Next, a solvent solution of one or more solvents is provided in step 42 and the molecule building blocks, substrate, and template molecule(s) are added to the solution in step 44 to form a matrix. The molecule building blocks, substrate, and template molecule(s) can be added to the solvent solution in any order or sequence depending on the purpose or type of imprinting system. Next, in step 46, the substrate containing the matrix is removed form the solvent solution which has since become a deposition solution. Finally, the substrate containing the matrix is rinsed in step 48 to extract the template molecule(s).

The method for making the molecular recognition matrix of the present invention shown in FIG. 5 may also further include the step of pre-modifying or pre-treating the surface of the substrate with one or more specific functional groups that interact with the molecule building blocks (step 50). In addition, the method shown in FIG. 5 may also further include the step of carrying out post-synthetic functionalization process to increase the affinity and/or selectivity of the imprinted substrate after exposing the imprinted substrate (step 52).

The molecular recognition matrix of the present invention has many applications including, but not limited to, use in concentration, solid state extraction, separation, sensors, drug synthesis, absorbance, delivery of drugs, and drug design.

In one exemplary application of the present invention, sensors can be created that have enhanced binding abilities with discrete molecules and enhanced abilities to discriminate between discrete molecules and other structures. For example, the method for making a molecular recognition matrix of the present invention can be used to make an acetic acid sensor.

The present invention has been described above with reference to various exemplary embodiments. However, those skilled in the art will recognize that changes and modifications may be made to the exemplary embodiments without departing from the scope of the present invention. For example, the various steps, as well as the components for carrying out the steps, may be implemented in alternate ways depending upon a particular application. These and other changes or modifications are intended to be included within the scope of the present invention, as set forth in the following claims.

The invention claimed is:

1. A method for making a molecular recognition matrix comprising, in order, the steps of:
providing one or more molecules for use as molecule building blocks and a substrate having a surface capable of interacting with the molecule building blocks;
providing one or more template molecules;
adding the molecule building blocks and the template molecules separately to one or more solvents to create a deposition solution wherein the molecule building blocks are soluble in the one or more solvents;
adding the substrate to the deposition solution to create a matrix via the interaction between the molecule building blocks and the surface of the substrate where the molecule building blocks interact with the surface of the substrate and there is no bonding between the molecule building blocks and the templates;
removing the substrate containing the matrix from the deposition solution; and
rinsing the substrate containing the matrix with a different one or more solvents or other solutions to extract the template molecules thereby creating an imprinted substrate.

2. The method of claim 1 further comprising the step of curing the imprinted substrate.

3. The method of claim 1 wherein the molecule building blocks comprise at least one of a monomer, a molecule, an ion, a polyatomic ion, a salt, a compound, a complex, a pure chemical element, an elemental molecule, and a crystal.

4. The method of claim 1 wherein the substrate comprises a solid material comprising at least one of a polymer, an optical fiber, a metal, a semiconductor, a glass, a plastic, an organic material, and an inorganic material.

5. The method of claim 1 wherein the substrate may comprise any shape.

6. The method of claim 1 wherein the substrate may comprise any size of material from bulk size materials to nanometer size materials.

7. The method of claim 1 wherein the template molecules comprise at least one or more kinds of molecules including one or more of a small molecule, a biological macromolecule, a microorganism, a crystal, a virus, or any material needing detection, separation, extraction, identification, capturing, or any other functional process.

8. The method of claim 1 wherein at least one molecular recognition cavity is formed on the surface of the substrate.

9. The method of claim 1 wherein the interaction between the substrate surface and the molecular building blocks comprises at least one of covalent bonding, non-covalent bonding, hydrophobic forces, van der walls forces, pi-pi interactions, ionic interactions, electrostatic effects, and other interactions that keep the template molecules within the matrix formed within the deposition solution.

10. The method of claim 1 wherein the interaction between the molecule building blocks and the surface of the substrate may be via polymerization, a self-assembling process, a polymerization after self-assembling process, an electro-polymerization, or other reaction process.

11. The method of claim 1 wherein the molecule building blocks are synthesized to have a specific function to interact with the surface of the substrate.

12. The method of claim 1 further comprising the step of pre-modifying or pre-treating the surface of the substrate with one or more specific functional groups that interact with the molecule building blocks.

13. The method of claim 1 further comprising the step of carrying out a post-synthetic functionalization process to increase at least one of the affinity and selectivity of the imprinted substrate after exposing the imprinted substrate.

14. A method for making a molecular recognition matrix comprising, in order, the steps of:
providing one or more molecules for use as molecule building blocks and a substrate having a surface capable of interacting with the molecule building blocks;
providing one or more template molecules;
adding the molecule building blocks and the template molecules to one or more solvents to create a deposition solution wherein the molecule building blocks are soluble in the one or more solvents;
adding the substrate to the deposition solution to create a matrix via the interaction between the molecule building blocks and the surface of the substrate where the molecule building blocks interact with the surface of the substrate and there is no bonding between the molecule building blocks and the templates;

removing the substrate containing the matrix from the deposition solution; and rinsing the substrate containing the matrix with a different one or more solvents or other solutions to extract the template molecules thereby creating an imprinted substrate.

* * * * *